United States Patent [19]
Hirschebain

[11] Patent Number: 5,865,183
[45] Date of Patent: Feb. 2, 1999

[54] DEVICE FOR EQUALIZING PRESSURE ACROSS THE EARDRUM OF DIVERS

[75] Inventor: Aviv Hirschebain, Tel Aviv, Israel

[73] Assignee: Safe Dive Ltd., Ramat Gan, Israel

[21] Appl. No.: 867,782

[22] Filed: Jun. 3, 1997

[51] Int. Cl.⁶ ...................................................... A61F 11/00
[52] U.S. Cl. ......................... 128/864; 181/130; 128/867
[58] Field of Search ................................... 128/864–868, 128/206.26; 181/130

[56] References Cited

U.S. PATENT DOCUMENTS

| | | | |
|---|---|---|---|
| 2,488,235 | 11/1949 | Pfeiffer . | |
| 2,719,523 | 10/1955 | Von Gierke | 128/864 |
| 2,876,767 | 3/1959 | Wasserman | 128/865 |
| 3,505,999 | 4/1970 | Harvey | 128/865 |
| 3,783,864 | 1/1974 | Moller | 128/864 |
| 4,406,282 | 9/1983 | Parker et al. . | |
| 4,553,627 | 11/1985 | Gastmeier | 128/864 |
| 4,896,380 | 1/1990 | Kamitani . | |
| 5,467,784 | 11/1995 | Mobley et al. . | |
| 5,483,975 | 1/1996 | Hirschenbain | 128/864 |

*Primary Examiner*—Michael A. Brown
*Attorney, Agent, or Firm*—Mark M. Friedman

[57] ABSTRACT

A device for facilitating the equalization of pressure across the eardrum of a user, comprising (a) an ear piece being sized and dimensioned for tightly fitting the outer ear canal of the user, such that when the user being underwater, water being prevented from entering between the ear piece and the outer ear canal, the ear piece being formed with a channel having an inner opening and an outer opening, the inner opening facing the eardrum of the user and the outer opening facing the outside, the channel and the outer ear defining a permanent void; and (b) an inflatable bag being in fluid communication with the ear piece via the outer opening, the bag defining a changeable void.

11 Claims, 3 Drawing Sheets

DEVICE FOR EQUALIZING PRESSURE ACROSS THE EARDRUM OF DIVERS

FIELD AND BACKGROUND OF THE INVENTION

The present invention relates to underwater diving equipment and, more particularly, to devices for facilitating the equalization of pressure between the diver's middle and outer ear and for preventing the outer ear from the influence of water and cold temperature while diving.

As shown in FIG. 1, the human ear is made up of three sections, commonly designated the outer ear, the middle ear and the inner ear. The outer ear includes the portion of the ear from the eardrum 10 outward to the ear opening. The inner ear includes the cochlea 12 and the three semi-circular canals 14. The middle ear is that portion of the ear between the eardrum 10 and the inner ear.

The middle ear is connected to the mouth cavity (not shown) through the eustachian tube 16, whose chief function is to equalize the pressure between the middle ear and the mouth cavity (typically the ambient pressure). Thus, under normal conditions, whenever the ambient pressure rises, the pressure in the outer ear rises, as does the pressure in the mouth cavity. The rise in pressure in the mouth cavity brings about a concomitant rise in the middle ear through the eustachian tubes. The result is adequate pressure equalization between the outer and middle ear across the eardrum (see FIG. 2).

The pressure equalization is particularly important for divers since the ambient pressure changes dramatically and rapidly as the diver lowers himself beneath the water surface or rises toward the water surface.

The pressure equalization may be delayed or prevented when secretions block the eustachian tubes (see FIG. 3). This may be the case when the diver's eardrum is excited by low temperatures, water or pressure which brings about edema with its excessive secretion from the mucous membranes surrounding the middle ear and the eustachian tube. The edema furthermore narrows the eustachian tubes.

Furthermore, when diving the pressure on the outer ear increases almost instantaneously while the pressure in the middle ear increases at a lower rate, because of the narrowness of the eustachian tubes, which causes, for a short time, a relative under-pressurized condition in the middle ear. This under-pressure can stimulate the secretion of mucous and blood from the tissue surrounding the middle ear and eustachian tube and could lead to the blockage of the eustachian and the prevention of further pressure stabilization.

The result of a pressure differential between the outer and middle ear can vary from discomfort to great pain and could, in some cases, lead to the rupture of the eardrum.

Additionally, it is desirable to prevent the entry of cold water into the ear, which could result in loss of balance, stimulated ear mucous and blood secretions and bacterial infections.

To prevent the pressure equalization and related difficulties, it has been proposed to prevent entrance of water into the ear and to provide external tubes which functionally supplement the eustachian tubes and which serve to equalize the pressure across the eardrum.

U.S. Pat. No. 4,896,380 discloses a facemask which is equipped with a pair of tubes. Each tube features an earplug at its far end. Each of the earplugs can be plugged into the ear canal and air from the facemask is able to reach the outer ear through the tube in order to equalize the pressure across the eardrum. A disadvantage of such a system is that the air pressure from the mask is transferred directly to the outer ear without any delay or attenuation which could cause the user considerable discomfort.

U.S. Pat. No. 2,488,235 also discloses an underwater facemask equipped with a pair of tubes. Each tube communicates at its far end with a substantially semi-spherical ear cup which covers the user's ear. The strap of the facemask serves to push the ear cups toward the user's ears. A disadvantage of such a system is that the strap securing the facemask to the face of the diver and the ear cups are essentially separate units so that the strap exerts inward pressure on the ear cups without relation to the ambient water pressure which destroys any chance of fine tuning the pressure on the user's ears, as described below. Furthermore, U.S. Pat. No. 2,488,235 fails to disclose a mechanism for adjusting the position of the ear cups to a specific user.

U.S. Pat. No. 5,483,975 teaches a device for facilitating the equalization of pressure across the eardrum of a user which typically includes a facemask configured to fit over at least the eyes and nose of the user. The device further includes a strap for securing the facemask to the face of the user. The strap, when secured to the head of the user, defines a single air space which includes ear portions overlying the user's ears and a connecting portion overlying the sides and back of the user's head and connecting the ear portions. Finally, the device includes a tube for supplying air to the air space. One end of the tube is connected to the air space while the other end of the tube is connected to a source of pressurized air, such as the facemask, the air supply controller or the air supply mouthpiece. A disadvantage of such a device is that the strap is traditionally used for tightly securing the mask to the user's face, such that it becomes water impermeable. Such a device requires also adjustments of the ear portions, such that they fit the position of the ears of a specific user. A mechanism for adjusting the position of the ear portions and for further tightly securing the mask to the users face requires both front and rear adjustments. However, due to the function of the strap as a single air space providing a rear adjustment is not feasible.

The above described prior art devices do solve some of the problems associated with diving, however, they call for replacing existing diving masks.

U.S. Pat. No. 4,406,282 teaches an earplug for use underwater which includes a tubular vessel of soft flexible material adapted for insertion into the ear canal. A disadvantage of such a device concerns the difficulty to insert the tubular vessel of soft flexible material into the ear canal. Additional disadvantage concerns the limited change in pressure which may be achieved in the outer ear using such a device. Furthermore, upon diving the change in pressure in the outer ear using this device is instantaneous, whereas the change in pressure in the middle ear is slower for reasons described hereinabove.

There is thus a widely recognized need for, and it would be highly advantageous to have, a simple and reliable device which will aid divers by equalizing the pressure between the outer and middle ear in a way which will minimize or eliminate discomfort.

SUMMARY OF THE INVENTION

According to the present invention there is provided a device for facilitating the equalization of pressure across the eardrum of a user, comprising (a) an ear piece being sized and dimensioned for tightly fitting the outer ear canal of the user, such that when the user being underwater, water being prevented from entering between the ear piece and the outer ear canal, the ear piece being formed with a channel having an inner opening and an outer opening, the inner opening facing the eardrum of the user and the outer opening facing the outside, the channel and the outer ear defining a permanent void; and (b) an inflatable bag being in fluid communication with the ear piece via the outer opening, the bag defining a changeable void.

According to still further features in the described preferred embodiments changeable void is at least four times larger in volume than the permanent void.

According to still further features in the described preferred embodiments the fluid communication is effected by a tube.

According to still further features in the described preferred embodiments the ear piece is made of a material selected from the group consisting of plastic, rubber, synthetic polymer and natural polymer.

According to still further features in the described preferred embodiments at least one region of the channel or tube is selected to have a small inner diameter such that the device is divided by the region into a first subspace adjacent to the ear and a second subspace removed from the ear, the inner diameter is selected such that when the ambient pressure is elevated and therefore the pressure within the second subspace rises, equilibration of pressure with the first subspace is delayed by a time period.

According to still further features in the described preferred embodiments the time period is within the range of one second and three minutes.

According to still further features in the described preferred embodiments the region includes a partition having an aperture.

According to still further features in the described preferred embodiments the partition is made of a flexible material.

According to still further features in the described preferred embodiments the region includes a filter.

According to still further features in the described preferred embodiments the device further comprising a mechanism for positioning the bag behind the external ear of the user.

According to still further features in the described preferred embodiments the device further comprising a mechanism for attaching the bag to a part of a diving mask.

According to still further features in the described preferred embodiments the mechanism includes a fastening tape consisting of opposing pieces that interlock when pressed together.

The present invention successfully addresses the shortcomings of the presently known configurations by providing a simple and reliable device for facilitating the equalization of pressure across the user's eardrums which is particularly useful during undersea diving.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a diving device which can be used to equalize pressure across the eardrum and to prevent the bad effects water and low temperature have on the ear while diving.

The principles and operation of a device according to the present invention may be better understood with reference to the drawings and the accompanying description.

Figure 1:
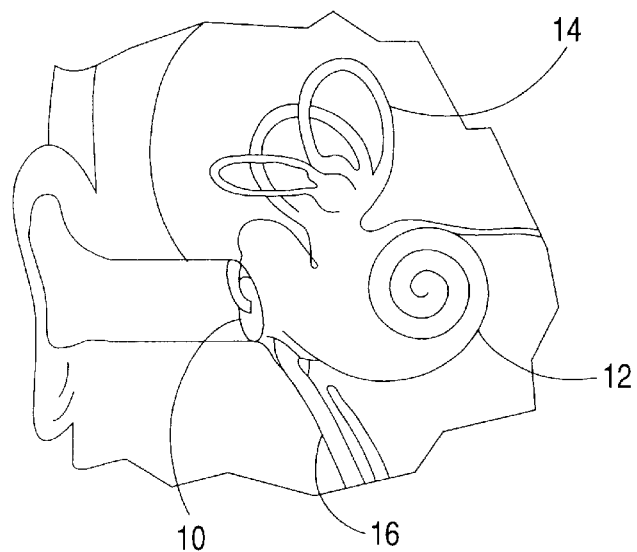
FIG. 1 is a cross-sectional view of the human ear.
Figure 2:
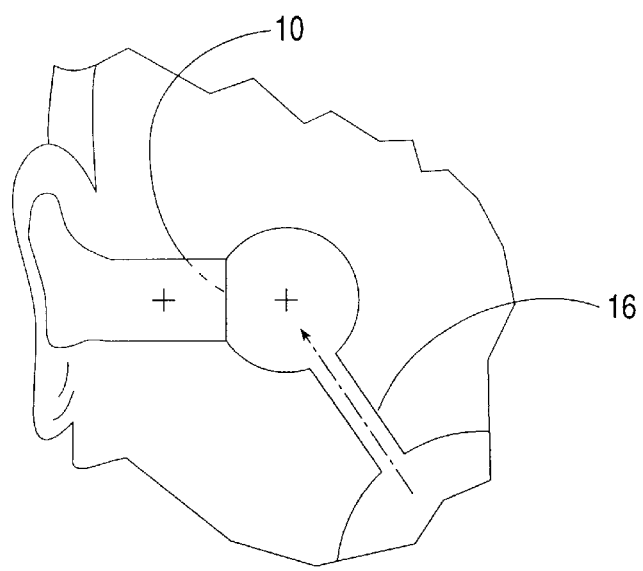
FIG. 2 is a schematic view of the human ear under pressure equalization.
Figure 3:
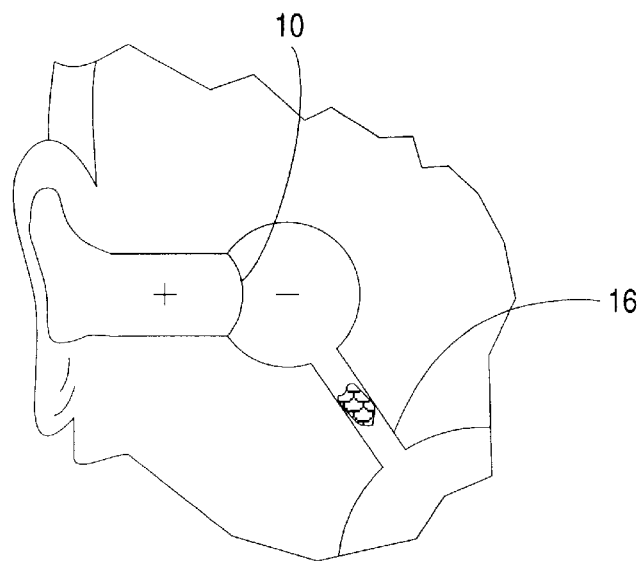
FIG. 3 is a schematic view of the human ear with a blocked eustachian tube which prevents pressure equalization.
Figure 5:
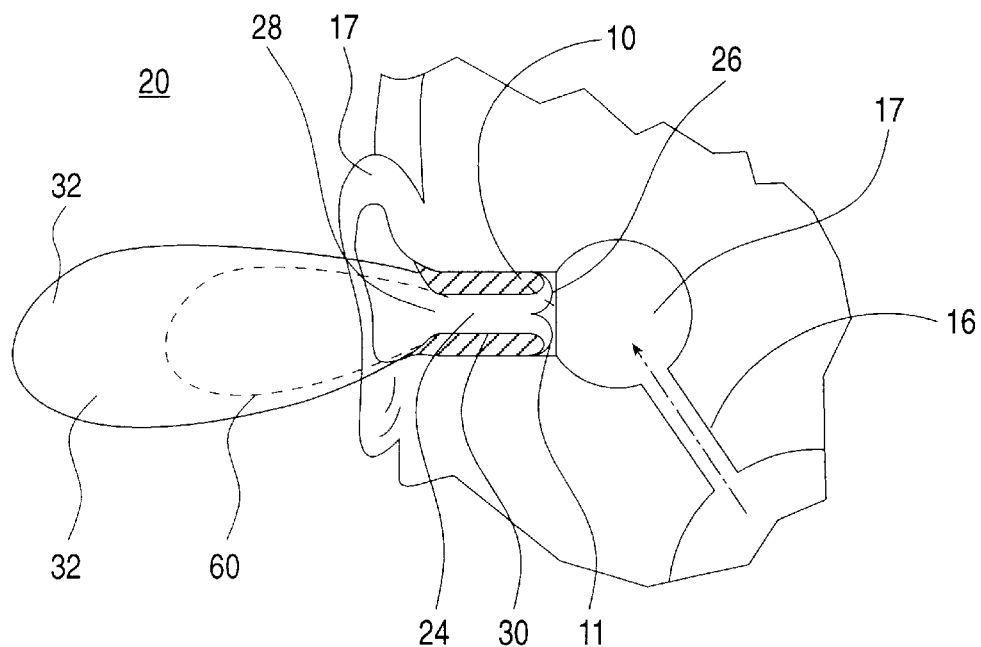
FIG. 5 is a cross section through the device according to the present invention when plugged within an outer ear of a user.
Figure 4:
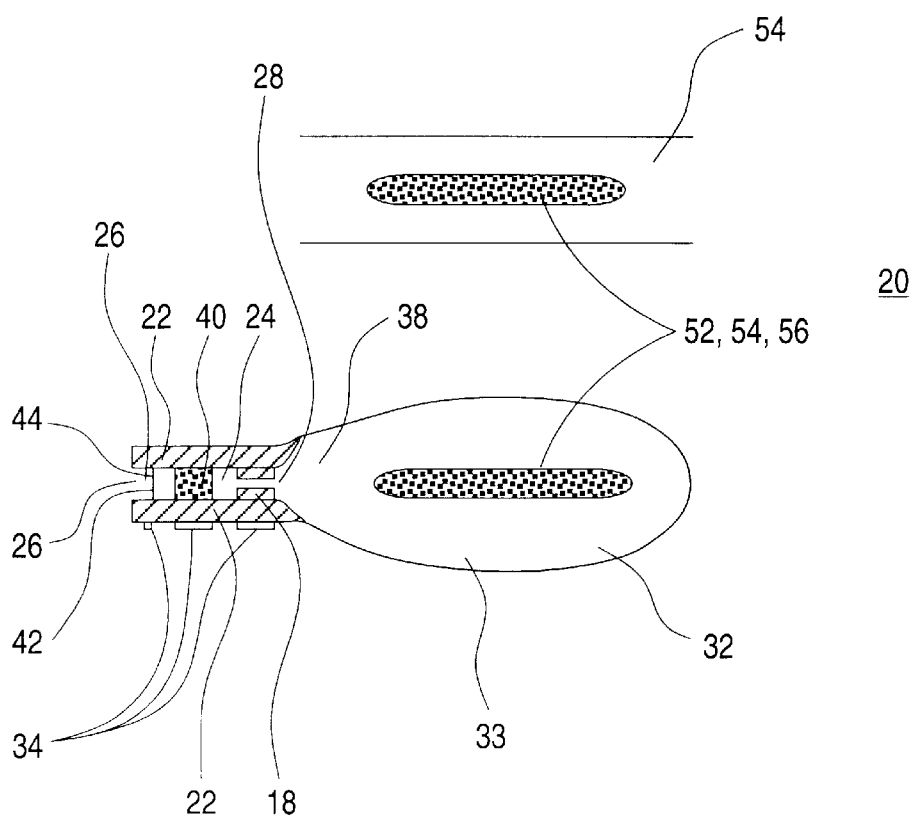
FIG. 4 is a cross section through a device according to the present invention.

Referring now to the drawings. FIG. 4 depicts a cross section through a device according to the present invention, referred to hereinbelow as device 20. FIG. 4 further depicts some preferred embodiments of device 20, according to the present invention. FIG. 5 depicts a cross section through device 20 when plugged in the outer ear canal of a user.

Device 20 serve for facilitating the equalization of pressure across the eardrum 10 of a user and includes an ear piece 22 sized and dimensioned to tightly fit the outer ear canal 11 of the user, such that when the user plugs ear piece 22 within outer ear canal 11 and dives underwater, water are prevented from entering between ear piece 22 and outer ear canal 11.

Ear piece 22 is formed with a longitudinal channel 24. Channel 24 has an inner opening 26 and an outer opening 28. Inner opening 26 faces eardrum 10 of the user, whereas outer opening 28 faces the outside. Channel 24 of ear piece 22 and outer ear canal 11 define a permanent void 30 which depends on the volume of channel 24 and the volume of canal 11 which remains unoccupied by ear piece 22.

Device 20 further includes an inflatable bag 32 which forms a fluid communication with channel 24 of ear piece 22 via outer opening 28. Bag 32 defines a changeable void 33 having a volume which depends upon the ambient pressure, as further described below.

Ear piece 22 may be made of any suitable material, including, but not limited to, plastic, rubber or any synthetic or natural polymer.

In a preferred embodiment of the invention at least one region 34 of channel 24 is selected to have a small inner diameter. In FIG. 4 three such regions 34 are presented as further described herein. In all cases, however, device 20 is divided by region(s) 34 into a first subspace 36 adjacent to the ear of the user and a second subspace 38 removed from the ear of the user.

The inner diameter of region(s) 34 is selected such that when the ambient pressure elevates and therefore the pressure within second subspace 38 rises, equilibration of pressure with first subspace 36 is delayed by a time period.

Thus, region(s) 34 ensure that when the ambient pressure changes, the change in pressure within the outer ear canal of the user changes gradually instead of instantly, as would otherwise be the case.

In a preferred embodiment of the invention the time period is selected within the range of one second and three minutes. The optimal pressure equilibration duration depends on the specific user and his eustachian tube (marked in FIG. 5 as 16) ability to equalize the pressure between the mouth cavity and the middle ear (marked in FIG. 5 as 17), as further described hereinabove in the Background section.

FIG. 4 presents three embodiments for a region 34.

According to the first, a thin capillary 38 is formed along at least a fraction of channel 24. The diameter of capillary 38 would determine the rate of pressure equilibration across it.

According to the second, a filter 40 is positioned within channel 24 of ear piece 22. Filter 40 is selected dense enough to delay pressure equilibration across it. One of ordinary skills in the art would know how to select filter 40 such that pressure equilibration will be delayed.

According to the third, a partition 42 formed with an aperture 44 is positioned within channel 24 of ear piece 22. In a preferred embodiment of the invention partition 42 is made of a flexible material. The size of aperture 44 would determine the rate of pressure equilibration across partition 42.

The purpose of region(s) 34 is to retard, in a controlled manner, the increase in pressure near the eardrum. Retarding the pressure increase prevents temporary under-pressure condition in the middle ear which reduces or eliminates the edema and secretions of the mucous in the middle ear.

The construction of region(s) 34 is selected so that the pressure in subspace 26 adjacent eardrum 10 does not rise instantaneously with increases in pressure in removed subspaces 28 but rather increases only gradually at a rate which is largely determined by the dimensions of the air passageway characterizing region(s) 34. This mimics the rise in pressure in the middle ear due to the narrow diameter and physiology behavior of eustachian tube 16.

Figure 6:
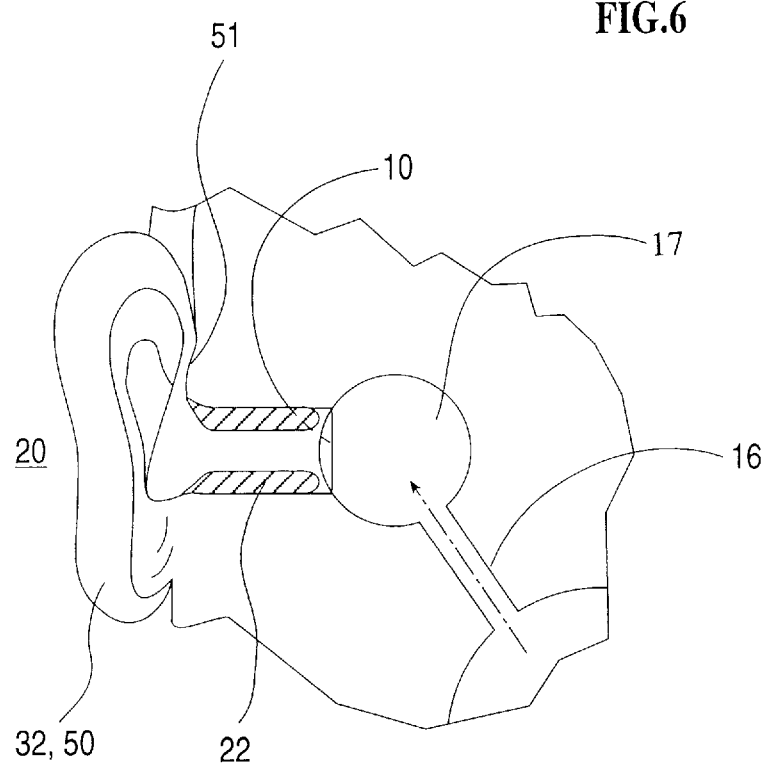
FIG. 6 is a cross section through the device according to the present invention when plugged within an outer ear of a user and having a mechanism for positioning the inflatable bag of the device behind the external ear of the user when used.

As shown in FIG. 6, according to a preferred embodiment of the invention, device 20 further includes a mechanism 50 for positioning bag 32 behind the external ear 17 of the user.

Mechanism 50 may be achieved, for example, by selecting the shape of bag 32 to be positioned behind external ear 32 when used, ensuring that even upon change in volume due to increase/decrease in ambient pressure, bag 32 will remain behind external ear 17.

As further shown in FIG. 6, in a preferred embodiment of the invention, fluid communication between bag 32 and channel 24 is effected by a tube 51. Tube 51 allows positioning of bag 32 away from the ear and may assist in preventing dislodging of ear piece 22 from the ear of the user due to movements imposed on bag 32 due to underwater streams, etc.

In addition, according to the present invention, any of regions 34 shown in FIG. 4, i.e., capillary 18, filter 40 and partition 42, which are used to divide device 20 into two subspaces, may be implemented within tube 51 instead of channel 24.

In a preferred embodiment of the invention ear piece 22, bag 32 and tube 51 of device 20 may be assembled/disassembled as desired.

As shown in FIG. 4, according to another preferred embodiment of the invention, device 20 includes a mechanism 52 for attaching bag 32 to a part of a diving mask (e.g., the rear strap) 54. Preferably, mechanism 52 includes a fastening tape 54 consisting of opposing pieces 56 that interlock when pressed together, e.g., VELCRO.

The operation of device 20 is as follows:

First the user selects a device that fit his/her special needs. These needs are determined both by the size of the user's ear canal and by the duration of preference for pressure equilibration. As mentioned above, the duration for pressure equilibrium may be controlled by control of the diameter of the air passageway within the channel of the ear piece of device 20.

Just before diving, the user carefully plugs the ear piece of device 20 into the ear canal. Should over pressure develop, due to the narrowed region(s) of the channel of the ear piece of device 20, the user may play with the ear piece to relieve that pressure. In any case, the user does so for each of his/her ears. At this point the pressure within both the adjacent and removed subspaces of device 20 equals the ambient pressure.

The user than starts to dive and as a result the ambient pressure instantly rises. The pressure within the breathing system of the user rises to equalize that of the surroundings by the air supply controller and the air supply mouthpiece of the diving equipment, as well known in the art. As a result, the pressure in the middle ear rises gradually via the eustachian tube, as explained in the Background section above. Concomitantly, the pressure within the remote subspace of device 20 rises, while the volume of the inflatable bag decreases. As a result of the narrowed region(s) of the channel of device 20, the pressure within the adjacent subspace and therefore the pressure close to the eardrum rises gradually instead of instantly, as would have otherwise been the case.

Such a construction ensures a substantially equal pressure across the eardrums of the user at all times during diving.

As shown in FIG. 5 by shaded line 60, while the ambient pressure changes, the volume of changeable void 33 changes while the volume of the permanent void 30 remains constant. Assuming that the maximal diving depth is about 50 meters, and that the change in ambient pressure is therefore about five atmospheres, and knowing that only the volume of void 30 changes while the ambient pressure changes, the following is preferably taken into account.

Defining void 30 as $V_1$ and void 33 as $V_2$, than:

$$V_1 + V_2 - \frac{V_1 + V_2}{5} < V_2, \text{ or } V_2 > 4V_1$$

should exist. Therefore, according to a preferred embodiment of the invention changeable void 33 is at least four times larger in volume than permanent void 30.

The device according to the present invention enjoys a number of advantages.

First it prevents water from entering the ear canal of the user and, as a result, it prevents the outer ear from the bad influence of water and cold temperature while diving.

Second, it equalizes the pressure across the eardrums while diving.

And finally, it fits to operate with existing diving masks and therefore does not require acquiring a new mask, as the prior art solutions described in the Background section above do.

While the invention has been described with respect to a limited number of embodiments, it will be appreciated that many variations, modifications and other applications of the invention may be made.

What is claimed is:

1. A device for facilitating the equalization of pressure across the eardrum of a user, comprising:

(a) an ear piece being sized and dimensioned for tightly fitting the outer ear canal of the user, such that when the user being underwater, water being prevented from entering between said ear piece and the outer ear canal, said ear piece being formed with a channel having an inner opening and an outer opening, said inner opening facing the eardrum of the user and said outer opening facing the outside, said channel and the outer ear defining a permanent void; and (b) an inflatable bag being in fluid communication with said ear piece via said outer opening, said bag defining a changeable void;

wherein at least one region of said channel is selected to have a small inner diameter such that the device is divided by said region into a first subspace adjacent to the ear and a second subspace removed from the ear, said inner diameter is selected such that when the ambient pressure is elevated and therefore the pressure within said second subspace rises, equilibration of pressure with said first subspace is delay by a time period, so that when the ambient pressure changes, the change in pressure within the outer ear canal of the user changes gradually instead of instantly, as would otherwise be the case.

2. The device of claim 1, wherein said fluid communication is effected by a tube.

3. The device of claim 1, wherein said ear piece is made of a material selected from the group consisting of plastic, rubber, synthetic polymer and natural polymer.

4. The device of claim 1, wherein said time period is within the range of one second and three minutes.

5. The device of claim 1, wherein said region includes a partition having an aperture.

6. The device of claim 5, wherein said partition is made of a flexible material.

7. The device of claim 1, wherein said region includes a filter.

8. The device of claim 1, further comprising a mechanism for positioning said bag behind the external ear of the user.

9. The device of claim 1, further comprising a mechanism for attaching said bag to a part of a diving mask.

10. The device of claim 9, wherein said mechanism includes a fastening tape consisting of opposing pieces that interlock when pressed together.

11. The device of claim 1, wherein said changeable void is at least four times larger in volume than said permanent void.

* * * * *